United States Patent
Gliner et al.

(10) Patent No.: US 6,353,758 B1
(45) Date of Patent: Mar. 5, 2002

(54) APPARATUS AND METHOD FOR DELIVERING A LOW ENERGY THERAPEUTIC PULSE TO A PATIENT

(76) Inventors: Bradford E Gliner, 4368 230th Way SE., Issaquah, WA (US) 98029; David B Cameron, 501 N. Aurora, Ithaca, NY (US) 14850; Dennis E Ochs, 2528 170th Pl. SE., Bellevue, WA (US) 98008

( * ) Notice: Subject to any disclaimer, the term of this patent is extended or adjusted under 35 U.S.C. 154(b) by 0 days.

(21) Appl. No.: 09/408,013

(22) Filed: Sep. 29, 1999

(51) Int. Cl.$^7$ .................................................. A61N 1/39
(52) U.S. Cl. ............................................................ 607/5
(58) Field of Search ................................ 607/5, 6, 7, 8, 607/9

(56) References Cited

U.S. PATENT DOCUMENTS

| | | | |
|---|---|---|---|
| 4,384,585 A | | 5/1983 | Zipes |
| 4,949,719 A | | 8/1990 | Pless et al. |
| 5,222,492 A | | 6/1993 | Morgan et al. |
| 5,314,448 A | | 5/1994 | Kroll et al. |
| 5,360,435 A | | 11/1994 | DeGroot |
| 5,366,485 A | | 11/1994 | Kroll et al. |
| 5,391,186 A | * | 2/1995 | Kroll et al. |
| 5,441,521 A | | 8/1995 | Hedberg |
| 5,766,226 A | * | 6/1998 | Pedersen |

FOREIGN PATENT DOCUMENTS

WO     WO99/37207     7/1999

OTHER PUBLICATIONS

Cleland; A Conceptual Basis for Defibrillation Waveforms; PACE, vol. 19, Aug. 1996; pp. 1186–1195.

Kroll; A Minimal Model of the Monophasic Defibrillation Pulse; PACE, vol. 16, Apr., Part I 1993; pp. 769–777.

Sweeney et al.; Defibrillation Using a High–Frequency Series of Monophasic Rectangular Pulses: Observations and Model Predictions; Journal of Cardiovascular Electrophysiology, vol. 7, No. 2, Feb. 1996; 134–143.

Walcott et al.; Choosing the Optimal Monophasic and Biphasic Waveforms for Ventricular Defibrillation; Journal of Cardiovascular Electrophysiology, vol. 6, No. 9, Sep. 1995; pp. 737–750.

Alferness et al.; The Influence of Shock Waveforms on Defibrillation Efficacy; IEEE Engineering in Medicine and Biology, Jun. 1990; pp. 25–27.

\* cited by examiner

Primary Examiner—Scott M. Getzow

(57) ABSTRACT

An electrotherapy method; and an apparatus for delivering electrotherapy to a patient. In particular, a method and apparatus for delivering a lower energy, therapeutically effective electrical waveform to a patient through a defibrillator. The method employed to lower the energy of the waveform can be applied to both internal defibrillators and external defibrillators. Further the method can be applied to any waveform, including monophasic, biphasic or multiphasic. Various custom shapes for a defibrillation waveform can be achieved by adjusting the rate at which the energy is duty cycled throughout any or all phases of the waveform.

27 Claims, 4 Drawing Sheets

APPARATUS AND METHOD FOR DELIVERING A LOW ENERGY THERAPEUTIC PULSE TO A PATIENT

BACKGROUND OF THE INVENTION

This invention relates generally to a method and apparatus for delivering a lower energy therapeutic pulse to a patient. Further this invention relates to a method and apparatus for shaping a delivered waveform by pulsing the energy delivered. More specifically, this invention relates to an electrotherapy method; and an apparatus for delivering electrotherapy to a patient. In particular, this invention relates to a method and apparatus for delivering a lower energy, therapeutically effective electrical waveform to a patient through a defibrillator. The method employed to lower the energy of the waveform can be applied to internal cardiac defibrillators (ICDs), automatic or semi-automatic external defibrillators (AEDs) and manual external defibrillators.

Sudden cardiac death is the leading cause of death in the United States. On average, 1000 people per day die; this translates into one death every two minutes. Most sudden cardiac death is caused by ventricular fibrillation ("VF"), in which the heart's muscle fibers contract without coordination, thereby interrupting normal blood flow to the body. The only effective treatment for VF is electrical defibrillation, which applies an electrical shock to the patient's heart. The electrical shock clears the heart of the abnormal electrical activity (in a process called "defibrillation") by depolarizing a critical mass of myocardial cells to allow spontaneous organized myocardial depolarization to resume.

To be effective, the defibrillation shock must be delivered to the patient within minutes of the onset of VF. Studies have shown that defibrillation shocks delivered within one minute after the onset of VF achieves up to a 100% survival rate. However, the survival rate falls to approximately 30% after only 6 minutes. Beyond 12 minutes, the survival rate approaches zero. Importantly, the more time that passes, the longer the brain is deprived of oxygen and the more likely that brain damage will result.

As would be expected, because external defibrillators deliver their electrotherapeutic pulses to the patient's heart indirectly (i.e., from the surface of the patient's skin rather than directly to the heart), they operate at higher energies, voltages and/or currents than ICDs. One consequence of using high energy, voltage and current is that external defibrillators have tended to be large, heavy and expensive, particularly due to the large size of the capacitors or other energy storage media required. Historically, the size and weight of external defibrillators has limited their utility for rapid response by emergency medical response teams. Additionally the higher energies used are associated with increased damage to the cardiac tissue.

Another disadvantage is that the shapes of the waveforms are a function of the components used to deliver the energy.

Yet another disadvantage of external defibrillators is that it may be subjected to extreme load conditions which could potentially damage the circuitry. For example, improperly applied defibrillator electrodes may create a very low impedance current path during the shock delivery, which could result in excessively high current within the waveform circuit. Thus, an external defibrillator has an additional design requirement to limit the peak current to safe levels in the waveform circuit, which is not normally a concern for implanted defibrillators.

Gliner et al., U.S. Pat. No. 5,607,454 entitled "Electrotherapy Method and Apparatus," describes an external defibrillator which is capable of delivering an impedance compensated biphasic waveform. The use of a biphasic waveform considerably lowers the energy required to defibrillate a patient from the standard 200-300-360J used in monophasic external defibrillators to 150J. This enables the device to achieve a lower weight (4 lbs.) than possible for traditional monophasic devices, which typically weigh in excess of 8 lbs. The advancements taught by Gliner et al. are embodied in the Heartstream ForeRunner® AED.

In further support of using lower energies, evidence has shown that higher energies, such as those typically used in delivering a monophasic waveform, can result in damage to the heart tissue—particularly where successive shocks are needed to defibrillate a patient. The use of the lower energy, such as those employed when delivering an impedance compensated biphasic waveform (as described by Gliner et al.), reduces the likelihood of damage to the heart tissue. Evidence received from professionals in emergency medicine also indicates that the physiological effect on a patient receiving the same number of defibrillation shocks from a monophasic vs. a biphasic defibrillator is significant. Specifically, the use of low energy biphasic waveforms provides significantly less post-resuscitation myocardial dysfunction.

Sweeney et al. conducted a study of the effect of high-frequency monophasic rectangular pulses delivered directly onto the pericardium. Sweeney et al. "Defibrillation Using A High-Frequency Series of Monophasic Rectangular Pulses: Observations and Model Predictions" J. Cardiovasc. Electrophys. 7(2): 1996. Sweeney concluded that defibrillation was possible using HF pulsed current waveform at frequencies as high as 20 kHz. From the results, Sweeney predicted that a 10 m-sec ascending ramp waveform will require 46% less energy than a 10 m-sec truncated exponential waveform.

Notwithstanding the great strides made in developing a lower energy, impedance compensated waveform. Improvements are still possible that would either lower the energy requirements even further without compromising the efficacy of the treatment or enable a variety of custom shaped waveforms to be delivered. What is needed, therefore, is a method of delivering energy to a patient that provides an efficacious therapeutic energy pulse while reducing the total amount of energy delivered. Further what is needed is a way to reduce the size of the components associated with the defibrillator.

SUMMARY OF THE INVENTION

In one embodiment, this invention provides a defibrillator and defibrillation method that delivers a lower energy waveform for administering a therapeutic shock to the cardiac muscle of a patient in VF. In another embodiment, the invention also allows the waveform to be shaped more accurately. In one specific embodiment, the invention provides a lower energy waveform that automatically compensates for patient-to-patient impedance differences in the delivery of electrotherapeutic pulses for defibrillation and cardioversion. In an even more preferred embodiment, the defibrillator has an energy source that may be discharged through electrodes on the patient to provide a biphasic voltage or current pulse. In one aspect of the invention, the first and second phase duration and initial first phase amplitude are predetermined values. This is achieved by duty cycling the voltage delivery so that it cycles between ON and OFF. Voltage cycling can be accomplished at a fixed frequency with a fixed pulse width. Alternatively, duty cycling of the voltage or current can be accomplished by providing a fixed frequency with a variable pulse width, or by providing a variable frequency with a fixed pulse width.

A method for delivering electrotherapy to a patient through electrodes, the method comprising the following steps: discharging an energy source across the electrodes to deliver electrical energy to the patient in at least one phase; wherein the discharging step is duty cycled during at least one phase at a frequency sufficient to generate a therapeutically efficacious voltage envelope. Additionally the discharging step may have a plurality of phases. The plurality of phases being biphasic. Optionally the discharging step may be cycled during more than one phase. Duty cycling can be performed at a constant frequency or at a variable frequency. Alternatively, or in addition, the pulse width of the duty cycle may be a constant width or a variable width. This method may be employed in an implantable cardiac defibrillator or an external defibrillator, more specifically an automatic external defibrillator.

Another method involves delivering electrotherapy to a patient through electrodes, the method comprising the following steps: discharging an energy source across the electrodes to deliver a electrical energy to the patient in at least one phase; wherein the discharging step is duty cycled during at least one phase at a frequency sufficient to generate a therapeutically efficacious average voltage. Additionally the discharging step may have a plurality of phases. The plurality of phases being biphasic. Optionally the discharging step may be cycled during more than one phase. Duty cycling can be performed at a constant frequency or at a variable frequency. Alternatively, or in addition, the pulse width of the duty cycle may be a constant width or a variable width. This method may be employed in an implantable cardiac defibrillator or an external defibrillator, more specifically an automatic external defibrillator.

An apparatus that performs these methods is also provided for. The apparatus delivers electrotherapy to a patient through one or more electrodes and comprises: a storage circuit operable to store electrical energy; a steering circuit coupled with the storage circuit, the steering circuit being adapted for coupling with the patient and operable to deliver the electrical energy from the storage circuit to the patient; and a switch operable to duty cycle the voltage delivered to the patient. As described in the method, the voltage duty cycle has a pulse width for each cycle and further wherein the voltage duty cycle is delivered at a frequency. Further, the steering circuit is capable of delivering energy to the patient in a plurality of phases. The switch is operable to duty cycle the voltage delivered to the patient at a constant frequency or a variable frequency.

The invention is described in more detail below with reference to the drawings.

BRIEF DESCRIPTION OF THE DRAWINGS

FIG. 1 illustrates three waveforms which are currently used for defibrillation.

FIG. 2 illustrates the three waveforms of FIG. 1 which have been modified according to the teachings of this invention.

DETAILED DESCRIPTION OF THE PREFERRED EMBODIMENT

The following discussion is presented to enable a person skilled in the art to make and use the invention. Various modifications to the preferred embodiment will be readily apparent to those skilled in the art, and the generic principles herein may be applied to other embodiments and applications without departing from the spirit and scope of the present invention as defined by the appended claims. Thus, the present invention is not intended to be limited to the embodiment show, but is to be accorded the widest scope consistent with the principles and features disclosed herein.

Figure 1A:
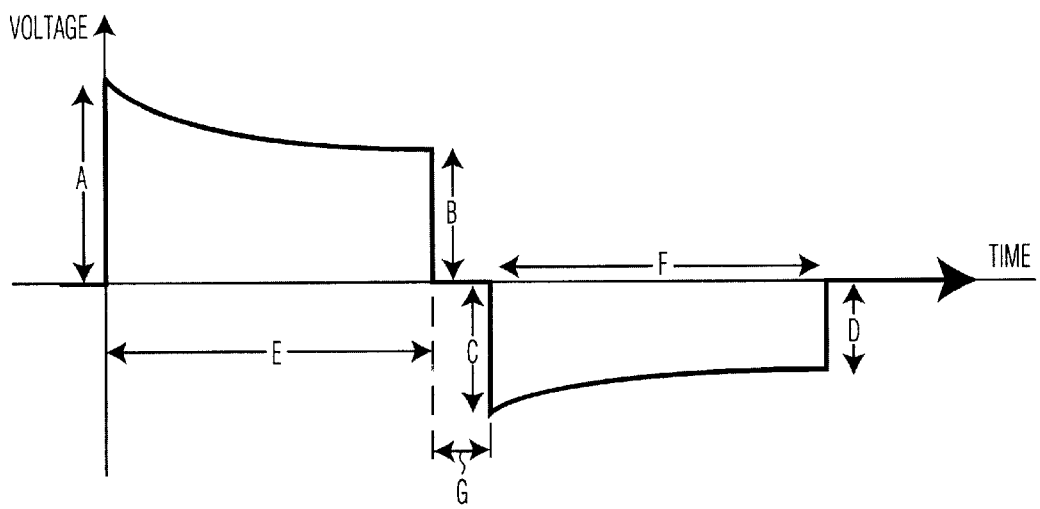
FIGS. 1A and 1B illustrate low-tilt and high-tilt biphasic electrotherapeutic.
Figure 1B:
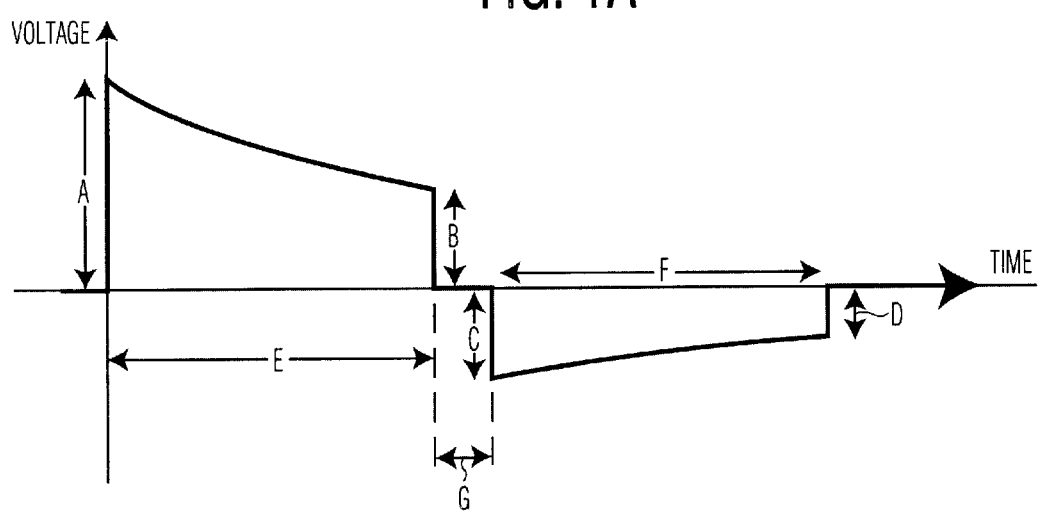

As discussed in Gliner et al. (U.S. Pat. No. 5,607,454), the specification of which is incorporated herein, FIGS. 1A and 1B illustrate a waveform that takes into account patient-to-patient impedance differences. These figures represent truncated exponential biphasic waveforms delivered to two different patients from an external defibrillator according to the electrotherapy method of this invention for defibrillation or cardioversion. In these drawings, the vertical axis is voltage, and the horizontal axis is time. When delivered external to the patient, the biphasic waveform shown in FIG. 1 typically takes between 5 and 20 mseconds to be delivered depending on patient impedance.

The waveform shown in FIG. 1A is a low-tilt waveform, and the waveform shown in FIG. 1B is a high-tilt waveform. As shown in FIGS. 1A and 1B, A is the initial first phase voltage and D is the second phase terminal voltage. The first phase terminal voltage B results from the exponential decay over time of the initial voltage A through the patient, and the second phase terminal voltage D results from the exponential decay of the second phase initial voltage C in the same manner. The starting voltages and first and second phase durations of the FIG. 1A and FIG. 1B waveforms are the same; the differences in end voltages B and D reflect differences in patient impedance.

Gliner et al. determined that, for a given patient, externally-applied truncated exponential biphasic waveforms defibrillate at lower voltages and at lower total delivered energies than externally-applied monophasic waveforms. In addition, Gliner et al. determined that there is a complex relationship between total pulse duration, first to second phase duration ratio, initial voltage, total energy and total tilt.

Figure 1C:
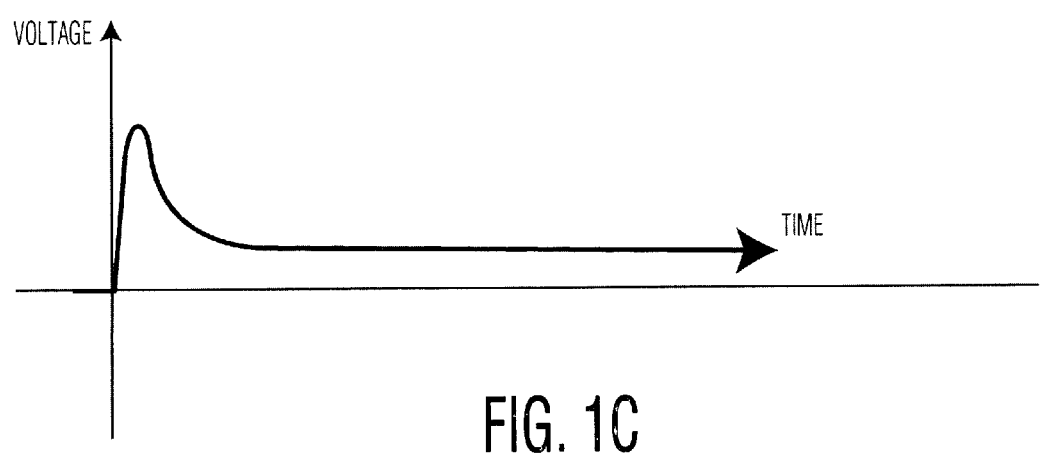
FIG. 1C is a damped sinusoid waveform which may be employed in a commercially available external defibrillator.

FIG. 1C is a damped sinusoid monophasic waveform. Monophasic waveforms are commonly used in commercially available external defibrillators. Delivery of a damped sinusoid monophasic waveform typically takes less than 20 mseconds. In delivering the monophasic energy pulse, the capacitor is charged to a desired energy level. Thereafter a relay or switch is closed to connect the capacitor to the patient and the energy passes through the patient. The resulting shape of the waveform is a function of: the capacitor, a wave shaping inductor and the patient resistance which together function as an RLC circuit.

In order to avoid obscuring the invention, applicants have omitted details regarding specific mechanisms employed to shape the waveform as well as the many types of waveform shapes that are currently used. A summary of waveforms is provided in Alferness et al. "The Influence of Shock Waveforms on Defibrillation Efficacy," IEEE Engineering in Medicine and Biology (June 1990), p. 25. However, achieving the energy reduction results of this invention can easily be achieved with a variety of waveforms taking into account a variety of shaping mechanisms. Another discussion of waveforms is also provided in Cleland "A Conceptual Basis for Defibrillation Waveforms" PACE 19:1186–1195 (1996).

Figure 2A:
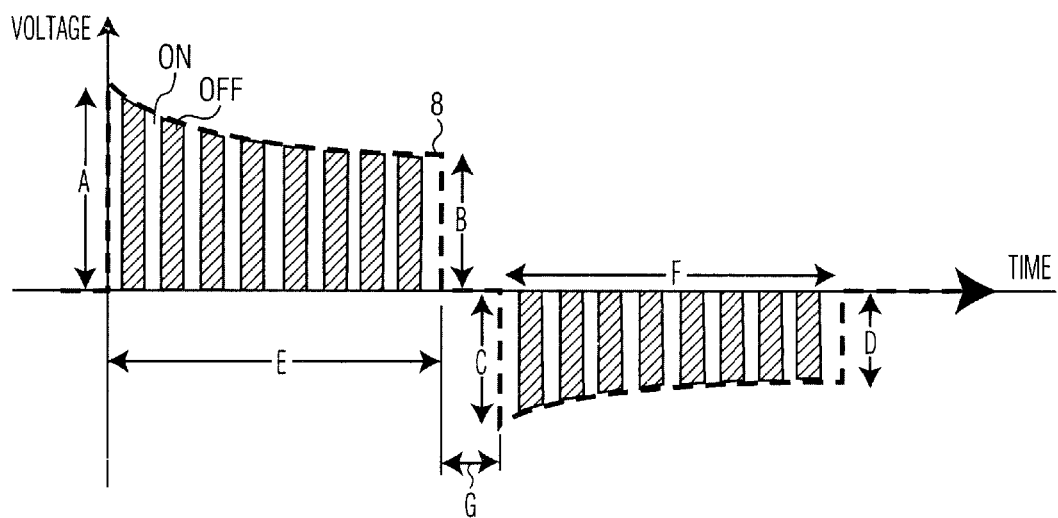
FIGS. 2A and 2B illustrate a duty-cycled low-tilt and high-tilt biphasic electrotherapeutic waveform.
Figure 2B:
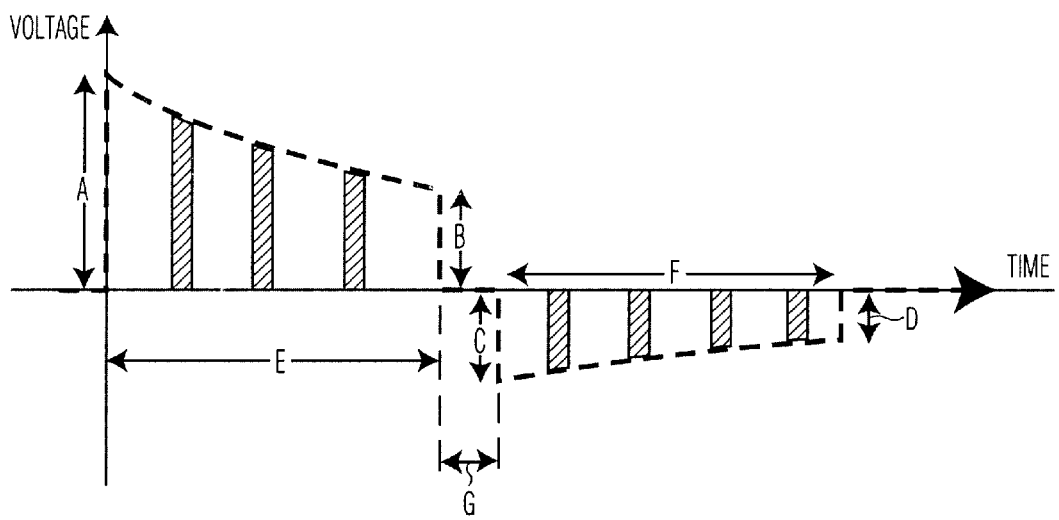

Turning now to FIGS. 2A and 2B, the waveform described by Gliner et al. has been modified according to this invention so that the effective shape of the waveform comprising the therapeutic energy pulse (or voltage envelope) is the same as that shown in respective FIGS. 1A and 1B (as shown by the dashed line 8). Significantly, however, the total amount of energy actually delivered is reduced as a result of a on/off cycling of the voltage delivered to the patient. This ON/OFF cycling may be referred to as "duty cycling" and results in the voltage being delivered in pulses. Each pulse has a pulse width corresponding to the time of the ON cycle. As will be appreciated by those of skill in the art, the total reduction of energy delivered will depend upon the ratio between the ON and OFF cycles of the duty cycle. Further, advantages may be obtained by duty cycling the voltage at a higher or lower frequencies.

Many permutations are possible in applying the invention to ICDs and external defibrillators. For example, one phase of a waveform could be duty cycled while another phase is not. Accordingly, the following examples are provided by way of illustration. It will be appreciated that many other embodiments are possible using the teachings of this application, although not specifically set forth.

For example, to reduce the total energy delivered of a biphasic defibrillation waveform, which normally delivers 150J of energy by 50%, the voltage delivery could be duty cycled at a fixed frequency so that the patient circuit would effectively be ON one-half of the time and OFF one-half of the time. As a result of cycling the voltage, the resulting voltage envelope would remain the same. For purposes of illustration, FIG. 2A has been shown to deliver 50% less energy with a relatively high rate of duty cycling. Thus, the total amount of energy delivered is reduced from 150J to 75J. As shown in FIG. 2A, each duty cycle of the voltage delivered has a constant pulse width and each duty cycle is delivered at a constant frequency.

In another example, again using a waveform that normally delivers 150J, in order to reduce the total energy delivered by 33%, the switch controlling the delivery of voltage delivery to the patient circuit would effectively be ON two-thirds of the time and OFF one-third of the time. Again, for purposes of illustration, each duty cycle of the voltage delivered has a constant pulse width and each duty cycle is delivered at a constant frequency. As a result of this illustration the total amount of energy delivered is reduced from 150J to 100J.

As will be appreciated by those of skill in the art, the ON/OFF pulsing of voltage delivery which creates a voltage envelope can be applied to any waveform delivered to a patient—whether internally or externally; monophasic, biphasic or multiphasic. The net result is that the total amount of energy delivered to the cardiac muscles is lowered. Further, instead of delivering the voltage or current at a constant frequency and a constant pulse width, either variable can be held constant while the other variable is modified. Thus, voltage could be delivered at a constant frequency while the pulse width is varied. Alternatively, voltage could be delivered at a constant pulse width while the frequency is varied.

Contrasting the waveforms of FIG. 1 with those of FIG. 2, the waveforms of FIG. 1 represent therapeutically effective energy pulses with a single cycle per phase of the waveform used in defibrillation. In contrast, the waveforms shown in FIG. 2 may be described as therapeutically effective energy pulses with a plurality of duty cycles per phase also used for defibrillation. In one embodiment, the duty cycles of the phase form a voltage envelope, the efficacy of which corresponds to the efficacy of the corresponding waveform shown in FIG. 1.

Figure 2C:
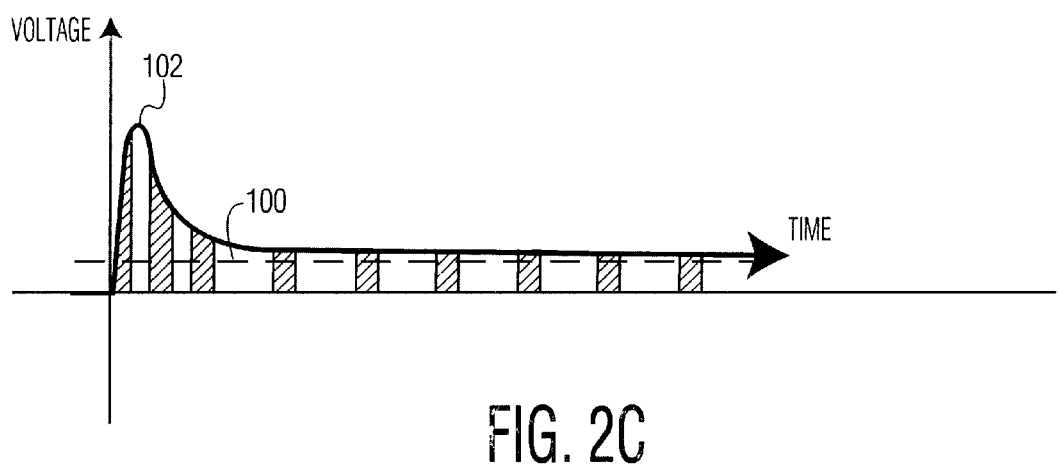
FIG. 2C is a duty-cycled damped sinusoid waveform.

In illustrating an alternative theory, FIG. 2C shows a damped sinusoid monophasic waveform which has been duty cycled to demonstrate that the average effect of the waveform 100. By cycling the voltage delivery at a higher frequency during the initial stage of the energy delivery and then cycling the voltage at a lower frequency during the later stage of energy delivery, the average effect (i.e., the average between the ON and OFF phases of the pulse) for the entire waveform results in a net shape 100 which differs from the voltage envelope 102.

As with the previous example, the ON/OFF pulsing of voltage delivery which creates the average voltage delivery can be applied to any waveform delivered to a patient, whether internally or externally; monophasic, biphasic or multiphasic.

Where voltage delivery is adjusted to create an average voltage delivery, the net result is that a variety of waveform shapes can be achieved. Such effective waveform shapes could, for example, have a specific linear slope.

Figure 3:
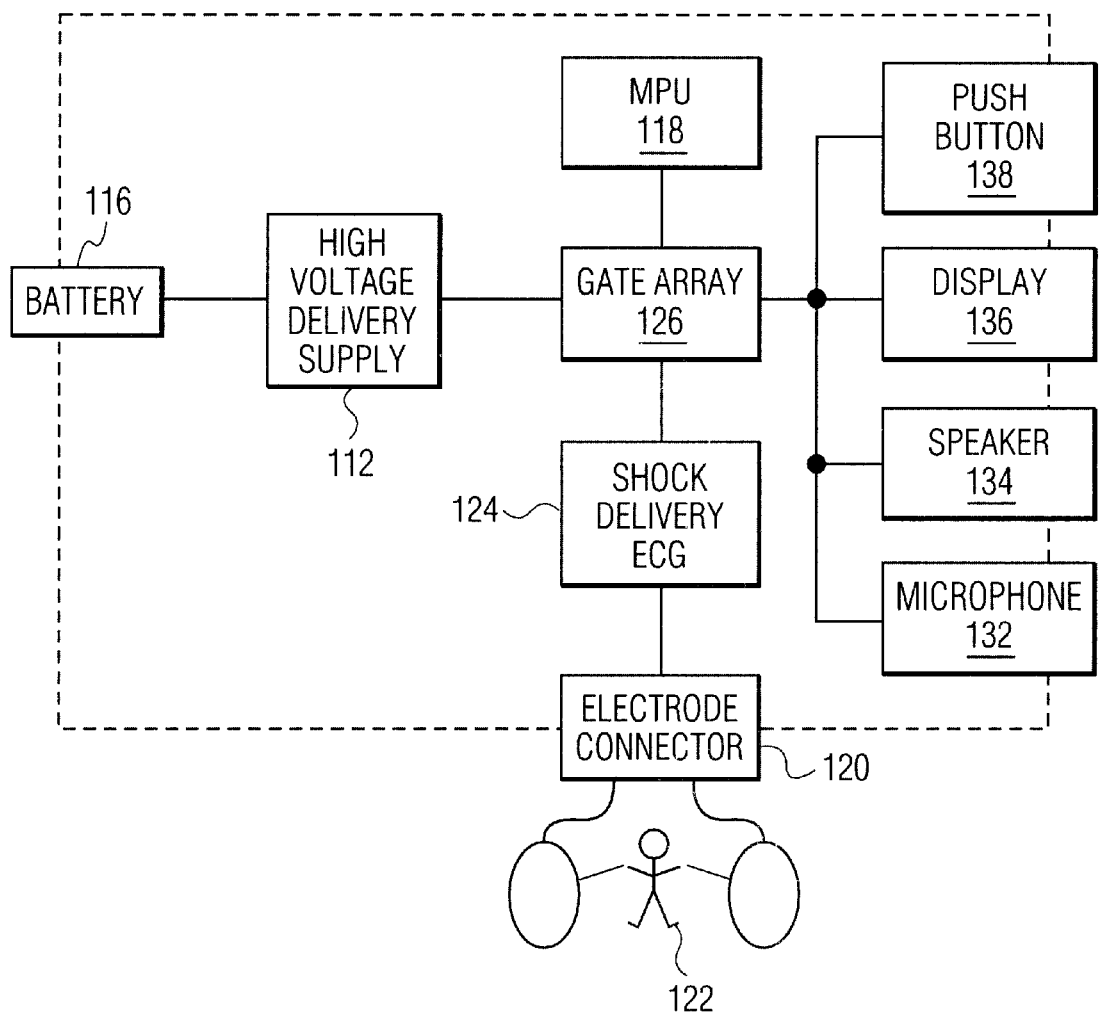
FIG. 3 is a functional block diagram of a defibrillator.

FIG. 3 is a functional block diagram depicting a defibrillator 110 having a high-voltage delivery circuit 112 in accordance with an embodiment of the present invention. The defibrillator 110 includes a power supply 114, which is powered by an energy source such as a removable battery 116 and provides power to other components of the defibrillator. A microcontroller or processor 118 controls the operation of the various components of the defibrillator 110. The high-voltage delivery circuit 112 delivers a pulse of electrical energy to a patient via an electrode connector or interface 120 and electrodes 122.

An electrocardiogram (ECG) circuit 124 acquires and processes the patient's ECG signals through the electrodes 122 and sends the signals to the processor 118 via a system gate array 126. The system gate array 126 is preferably a custom application-specific integrated circuit (ASIC) integrating many of the defibrillator functions (including user interface control and many of the internal functions) and interfacing the processor 118 with other components of the defibrillator 110. Providing the separate system gate array or ASIC 126 allows the processor 118 to focus on other tasks. Of course, the functionality of the ASIC 126 could be included within the operations performed by the processor 118, or could be replaced by discrete logic circuit components or a separately dedicated processor.

The defibrillator 110 also includes a memory device 130. The memory device 130 enables the defibrillator 110 to store data. The memory device may be permanently associated with the defibrillator, or removable. Where the memory device is permanently associated, a mechanism is provided to remove the data. Such a mechanism could include, for example, a serial port or an IRDA link. As depicted in FIG. 1, memory device 130 is a removable PCMCIA card or magnetic tape. Defibrillator 110 also includes user interface components such as a microphone 132, an audio speaker 134, an LCD display panel 136, and a set of push-button controls 138. Those skilled in the art will understand that a number of other components are included within the defibrillator 110 (e.g., a system monitor and associated status indicators), but are not shown in order to avoid unnecessarily obscuring the description of embodiments of the invention.

Figure 4:
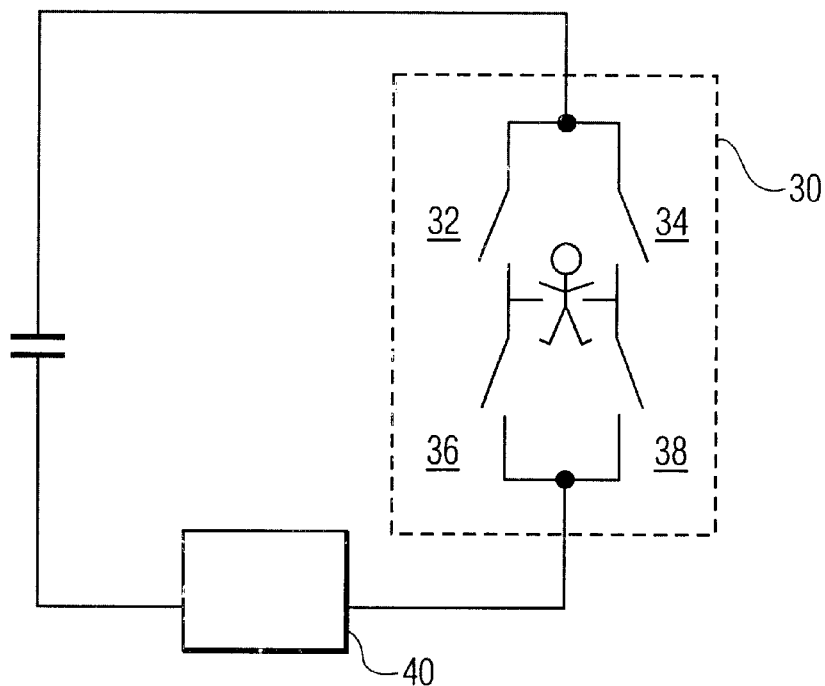
FIG. 4 is a schematic diagram showing a circuit capable of delivering a biphasic waveform of the invention.

FIG. 4 is a schematic diagram showing a circuit for delivery of a biphasic or multiphasic waveform of the invention. As shown a defibrillator system 110 has an energy source, illustrated here as capacitor 112. Where the circuit is delivering an external duty cycled shock, a corresponding reduction to the size of the capacitor can be accomplished. For example, the capacitor size could be reduced from 105 $\mu$F to between 25 and 90 $\mu$F, most preferably between 40 and 60 $\mu$F. The system also includes a charging mechanism (not shown) for charging the capacitor to an initial voltage. Where the circuit is delivering a duty cycled shock in an ICD, the preferred size of the capacitor is reduced from 100 $\mu$F to less than 60 $\mu$F.

A controller 124 controls the operation of the defibrillator to deliver a shock to the patient 126 through electrodes 128 automatically in response to a detected arrhythmia or manually in response to a human operator. FIG. 3 shows an ECG system 124 attached to the electrodes to provide ECG monitoring and/or arrhythmia detection. The ECG system is not an essential part of this invention.

A connecting mechanism 30 includes four switches 32, 34, 36 and 38 operated by the controller 24 to deliver a shock from the energy source 12 to the patient. The operation of the isolation connecting mechanism 30 to deliver a waveform to the patient is described below.

For purposes of this description, it is assumed that all switches are open prior to discharge. In response to a request for a shock, the controller 24 first closes switches 32 and 38, to begin delivery of a first phase of an electrotherapeutic pulse to the patient 26. Switches 32 and 38 are then opened and closed a plurality of times during the phase. The opening and closing of switches 32 and 38 will be accomplished to create a duty cycle. Preferably the integrity of the voltage envelope will be delivered such that while there is a reduction in the total amount of energy delivered, the voltage remains the same. A current sensor 40 may be used monitor the current delivered by the capacitor.

After delivery of the first phase of the waveform, the controller 24 then opens switches 32 and 38, and closes switches 34 and 36 to begin delivery of a second phase of an electrotherapeutic pulse to the patient 26. Switches 34 and 36 are then opened and closed a plurality of times during the phase. The opening and closing of switches 34 and 36 will be accomplished to create a duty cycle. Again it is preferred to maintain the integrity of the voltage envelope such that while there is a reduction in the total amount of energy delivered, the voltage remains the same. A current sensor 40 may be used monitor the current delivered by the capacitor.

This process may be repeated a plurality of times in order to generate a waveform with more than two phases.

Figure 5:
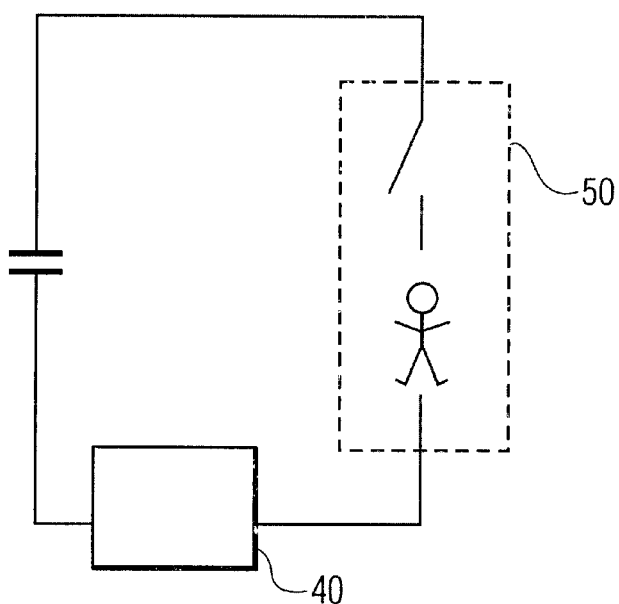
FIG. 5 is a schematic diagram showing a circuit capable of delivering a monophasic waveform of the invention.

FIG. 5 is a schematic diagram showing a circuit for delivery of a monophasic waveform. As shown a defibrillator system 10 has an energy source or capacitor 12. Where the circuit is delivering an external duty cycled shock, the preferred size of the capacitor is reduced from 35 $\mu$F to between 10 and 25 $\mu$F, most preferably between 15 and 20 $\mu$F. The system also includes a charging mechanism (not shown) for charging the capacitor to an initial voltage. Given the state of the art in ICDs it is not likely that a duty cycled monophasic waveform would be employed in an ICD, although it is a possible alternative embodiment under the teachings of this application.

A controller 24 controls the operation of the defibrillator to deliver a shock to the patient 26 through electrodes 28 automatically in response to a detected arrhythmia or manually in response to a human operator. FIG. 5 shows an ECG system 100 attached to the electrodes to provide ECG monitoring and/or arrhythmia detection. The ECG system is not an essential part of this invention.

A connecting mechanism 50 is operated by the controller 24 to deliver a shock from the energy source 12 to the patient. The operation of the connecting mechanism 50 to deliver a waveform to the patient is described below.

For purposes of this description, it is assumed that all switches are open prior to discharge. In response to a request for a shock, the controller 24 closes switch 50, to begin delivery of the monophasic electrotherapeutic pulse to the patient 26. Switch 50 is then opened and closed a plurality of times during delivery of the phase. The opening and closing of switch 50 creates a duty cycle. Preferably the integrity of the voltage envelope will be delivered such that while there is a reduction in the total amount of energy delivered, the voltage remains the same.

In a preferred embodiment of the circuit of either FIG. 4 or FIG. 5, solid state switching is employed to control the pulsed delivery of voltage. In some situations silicon controlled rectifiers (SCRs) may be employed in the circuit design provided that the SCRs will turn off quickly enough to prevent an over-current condition. Better performance will be obtained using solid state switching devices that are capable of turning on and off at a high rate, for example, insulated gate bipolar transistors (IGBTs) since IGBTs are known to turn off quickly and completely. The rate of cycling will result in delivery of a therapeutically effective energy pulse comprised of a plurality of cycles.

It should be understood that one or more capacitors may be used; for example a serial capacitor arrangement could be employed.

Devices operating according to this invention can be set-up to operate in a variety of ways. For example, an external defibrillator could be pre-programmed to deliver a duty cycled waveform at a particular phase rate. This would typically result if the waveform were employed in an AED. Alternatively, the AED could be set-up so that the AED delivers the lower energy duty cycled shock, but subsequently changes the shock, either by increasing the ON rate, or eliminating the duty cycling, in response to the resulting cardiac signal. Thus, the AED could deliver a range of energies to a patient.

Where duty cycling is employed by a manual defibrillator, the device may be set-up so that the operator selects the percentage of voltage delivery desired (for example 50%). In response to the operator selection, the defibrillator then duty cycles the voltage delivered at a pre-determined phase rate. If the operator determines that the resulting energy delivery was not sufficient, the operator could then change the amount or rate of cycling or eliminate the cycling all together. Additional control may, of course, be provided over the number of Joules such that the operator may select a 50% duty cycle of 300J. An operator may also be giving control over the rate of cycling within the phase.

Where duty cycling is employed in an ICD, the doctor may customize the amount of duty cycling as well as the phase rate at the time that the device is implanted. Additional control may be provided in the logic controlling delivery of the waveform such that if delivery of the first shock is not successful the ICD may automatically adjust the percentage of duty cycling or the phase rate to provide a more efficacious waveform.

The contents of references cited above is incorporated herein by reference.

As will be appreciated by those of skill in the art, other arrangements and operating algorithms are possible. It is understood that the various modifications and substitutions may be made by those of skill in the art without departing from the scope of the invention, which is defined in the claims below.

What is claimed is:

1. A method for delivering electrotherapy to a patient through electrodes external to the patient, the method comprising the following steps:

discharging an energy source across the electrodes external to the patient to deliver electrical energy to the patient in at least one phase;

duty cycling the discharging during at least one phase at a frequency sufficient to generate a therapeutically efficacious voltage envelope; and varying the duty cycle and the frequency during the electrotherapy to maintain therapeutic efficacy.

2. The method of claim 1 wherein the discharging step has a plurality of phases.

3. The method of claim 2 wherein the plurality of phases is biphasic.

4. The method of claim 2 wherein the discharging step is cycled during more than one phase.

5. The method of claim 1 wherein the discharging step is duty cycled at a constant frequency.

6. The method of claim 1 wherein the discharging step is duty cycled at a variable frequency.

7. The method of claim 1 wherein the duty cycle has a pulse width and the pulse width for each duty cycle of the discharging step is constant.

8. The method of claim 1 wherein the duty cycle has a pulse width and the pulse width for each duty cycle of the discharging step is variable.

9. The method of claim 1 wherein the energy is delivered to the patient internally by an implantable cardiac defibrillator.

10. The method of claim 1 wherein the energy is delivered to the patient externally by an external defibrillator.

11. The method of claim 10 wherein the external defibrillator is an automatic external defibrillator.

12. A method for delivering electrotherapy to a patient through electrodes external to the patient, the method comprising the following steps:

discharging an energy source across the electrodes external to the patient to deliver a electrical energy to the patient in at least one phase;

duty cycling the discharging during at least one phase at a frequency sufficient to generate a therapeutically efficacious average voltage; and varying the duty cycle and the frequency during the electrotherapy to maintain the therapeutically efficacious average voltage.

13. The method of claim 12 wherein the discharging step has a plurality of phases.

14. The method of claim 13 wherein the plurality of phases is biphasic.

15. The method of claim 13 wherein the discharging step is cycled during more than one phase.

16. The method of claim 13 wherein the discharging step is duty cycled at a constant frequency.

17. The method of claim 13 wherein the discharging step is duty cycled at a variable frequency.

18. The method of claim 13 wherein the duty cycle has a pulse width and the pulse width for each duty cycle of the discharging step is constant.

19. The method of claim 13 wherein the duty cycle has a pulse width and the pulse width for each duty cycle of the discharging step is variable.

20. The method of claim 13 wherein the energy is delivered to the patient internally by an implantable cardiac defibrillator.

21. The method of claim 13 wherein the energy is delivered to the patient externally by an external defibrillator.

22. The method of claim 21 wherein the external defibrillator is an automatic external defibrillator.

23. An apparatus for delivering electrotherapy to a patient through one or more electrodes external to the patient, the apparatus comprising:

a storage circuit operable to store electrical energy;

a steering circuit coupled with the storage circuit, the steering circuit being adapted for coupling with the patient and operable to deliver the electrical energy from the storage circuit to the patient;

a switch operable to duty cycle the voltage delivered to the patient; and circuitry for varying the duty cycle and the frequency during the electrotherapy to maintain the therapeutically efficacious average voltage.

24. The apparatus of claim 23 wherein the voltage duty cycle has a pulse width for each cycle and further wherein the voltage duty cycle is delivered at a frequency.

25. The apparatus of claim 24 wherein the steering circuit is capable of delivering energy to the patient in a plurality of phases.

26. The apparatus of claim 24 wherein the switch is operable to duty cycle the voltage delivered to the patient at a constant frequency.

27. The apparatus of claim 25 wherein the switch is operable to duty cycle the voltage delivered to the patient at a variable frequency during at least one phase.

* * * * *